United States Patent
Scheib

(10) Patent No.: US 10,285,700 B2
(45) Date of Patent: May 14, 2019

(54) SURGICAL STAPLE CARTRIDGE WITH HYDRAULIC STAPLE DEPLOYMENT

(71) Applicant: Ethicon Endo-Surgery, LLC, Guaynabo, PR (US)

(72) Inventor: Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 413 days.

(21) Appl. No.: 15/133,364

(22) Filed: Apr. 20, 2016

(65) Prior Publication Data

US 2017/0303924 A1 Oct. 26, 2017

(51) Int. Cl.
| | |
|---|---|
| A61B 17/10 | (2006.01) |
| A61B 17/068 | (2006.01) |
| A61B 17/00 | (2006.01) |
| A61B 17/072 | (2006.01) |

(52) U.S. Cl.
CPC .......... *A61B 17/105* (2013.01); *A61B 17/068* (2013.01); *A61B 17/072* (2013.01); *A61B 2017/00539* (2013.01); *A61B 2017/0725* (2013.01); *A61B 2017/07242* (2013.01); *A61B 2017/07271* (2013.01); *A61B 2017/07278* (2013.01)

(58) Field of Classification Search
CPC .................................................. A61B 17/105
USPC ....................................................... 227/177.1
See application file for complete search history.

(56) References Cited

U.S. PATENT DOCUMENTS

| | | | |
|---|---|---|---|
| 4,805,823 A | 2/1989 | Rothfuss | |
| 5,275,165 A * | 1/1994 | Ettinger | A61N 7/02 |
| | | | 600/411 |
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |

(Continued)

FOREIGN PATENT DOCUMENTS

| | | |
|---|---|---|
| EP | 1 785 097 A2 | 5/2007 |
| WO | WO 02/17799 A1 | 3/2002 |

OTHER PUBLICATIONS

International Search Report and Written Opinion dated Jul. 13, 2017 for Application No. PCT/US2017/027945, 15 pgs.

(Continued)

*Primary Examiner* — Alexander M Valvis
*Assistant Examiner* — Lucas E. A. Palmer
(74) *Attorney, Agent, or Firm* — Frost Brown Todd LLC

(57) ABSTRACT

A surgical instrument includes a body assembly, a shaft assembly, and an end effector. The end effector has first and second jaws that are configured to receive a tissue therebetween. The end effector also includes a staple cartridge including a plurality of staples and a hydraulic expandable member that is configured to receive a fluid and thereby expand from a contracted state to an expanded state. The hydraulic expandable member is further configured to direct at least one of the plurality of staples toward an anvil of the first jaw for forcing the at least one of the staples against the anvil and forming the at least one of the staples within the tissue.

20 Claims, 10 Drawing Sheets

(56) References Cited

U.S. PATENT DOCUMENTS

| | | | |
|---|---|---|---|
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 6,978,921 | B2 | 12/2005 | Shelton et al. |
| 7,000,818 | B2 | 2/2006 | Shelton et al. |
| 7,143,923 | B2 | 12/2006 | Shelton et al. |
| 7,246,734 | B2 | 7/2007 | Shelton, IV |
| 7,303,108 | B2 | 12/2007 | Shelton |
| 7,367,485 | B2 | 5/2008 | Shelton et al. |
| 7,380,695 | B2 | 6/2008 | Doll et al. |
| 7,380,696 | B2 | 6/2008 | Shelton et al. |
| 7,404,508 | B2 | 7/2008 | Smith et al. |
| 7,434,715 | B2 | 10/2008 | Shelton et al. |
| 7,524,320 | B2 | 4/2009 | Tierney et al. |
| 7,691,098 | B2 | 4/2010 | Wallace et al. |
| 7,721,930 | B2 | 5/2010 | McKenna et al. |
| 7,806,891 | B2 | 10/2010 | Nowlin et al. |
| 8,141,762 | B2 | 3/2012 | Bedi et al. |
| 8,210,411 | B2 | 7/2012 | Yates et al. |
| 8,371,491 | B2 | 2/2013 | Huitema et al. |
| 8,408,439 | B2 | 4/2013 | Huang et al. |
| 8,453,914 | B2 | 6/2013 | Laurent et al. |
| 8,479,969 | B2 | 7/2013 | Shelton |
| 8,573,461 | B2 | 11/2013 | Shelton et al. |
| 8,573,465 | B2 | 11/2013 | Shelton |
| 8,602,288 | B2 | 12/2013 | Shelton |
| 8,616,431 | B2 | 12/2013 | Timm et al. |
| 8,783,541 | B2 | 7/2014 | Shelton et al. |
| 8,800,838 | B2 | 8/2014 | Shelton |
| 8,801,735 | B2 | 8/2014 | Shelton et al. |
| 8,820,605 | B2 | 9/2014 | Shelton |
| 8,844,789 | B2 | 9/2014 | Shelton et al. |
| 8,955,732 | B2 | 2/2015 | Zemlok et al. |
| 9,186,142 | B2 | 11/2015 | Fanelli et al. |
| 9,198,644 | B2 | 12/2015 | Balek et al. |
| 9,301,759 | B2 | 4/2016 | Spivey et al. |
| 9,398,911 | B2 | 7/2016 | Auld |
| 2002/0062136 | A1* | 5/2002 | Hillstead ......... A61B 17/07207 606/205 |
| 2003/0045900 | A1* | 3/2003 | Hahnen ........... A61B 17/07207 606/205 |
| 2007/0102473 | A1* | 5/2007 | Shelton, IV ..... A61B 17/07207 227/175.1 |
| 2007/0106317 | A1* | 5/2007 | Shelton, IV ..... A61B 17/07207 606/170 |
| 2007/0125826 | A1* | 6/2007 | Shelton, IV ..... A61B 17/07207 227/175.1 |
| 2008/0169328 | A1 | 7/2008 | Shelton |
| 2008/0296346 | A1* | 12/2008 | Shelton, IV ..... A61B 17/07207 227/180.1 |
| 2008/0300580 | A1* | 12/2008 | Shelton, IV ..... A61B 17/07207 606/1 |
| 2011/0301604 | A1* | 12/2011 | Horner ................. A61B 17/29 606/52 |
| 2012/0080493 | A1* | 4/2012 | Shelton, IV ..... A61B 17/07207 227/176.1 |
| 2012/0228358 | A1* | 9/2012 | Zemlok ............... A61B 17/072 227/176.1 |
| 2013/0206813 | A1 | 8/2013 | Nalagatla |
| 2014/0205637 | A1* | 7/2014 | Widenhouse .... A61B 17/07292 424/400 |
| 2014/0239036 | A1 | 8/2014 | Zerkle et al. |
| 2014/0239037 | A1 | 8/2014 | Boudreaux et al. |
| 2014/0239038 | A1 | 8/2014 | Leimbach et al. |
| 2014/0239040 | A1 | 8/2014 | Fanelli et al. |
| 2014/0239041 | A1 | 8/2014 | Zerkle et al. |
| 2014/0239042 | A1 | 8/2014 | Simms et al. |
| 2014/0239043 | A1 | 8/2014 | Simms et al. |
| 2014/0239044 | A1 | 8/2014 | Hoffman |
| 2014/0263563 | A1 | 9/2014 | Stokes et al. |
| 2015/0272575 | A1 | 10/2015 | Leimbach et al. |
| 2015/0351754 | A1 | 12/2015 | Harris et al. |
| 2015/0351763 | A1 | 12/2015 | Shelton et al. |
| 2015/0351764 | A1* | 12/2015 | Shelton, IV ..... A61B 17/00491 227/176.1 |
| 2015/0374360 | A1 | 12/2015 | Scheib et al. |
| 2015/0374373 | A1 | 12/2015 | Rector et al. |
| 2016/0089146 | A1 | 3/2016 | Harris et al. |
| 2016/0166249 | A1* | 6/2016 | Knodel ............ A61B 17/07207 227/177.1 |
| 2017/0303925 | A1* | 10/2017 | Scheib ................. A61B 17/068 |

OTHER PUBLICATIONS

European Search Report, Extended, and Written Opinion dated Jul. 13, 2017 for Application No. EP 17167147.2, 10 pgs.

* cited by examiner

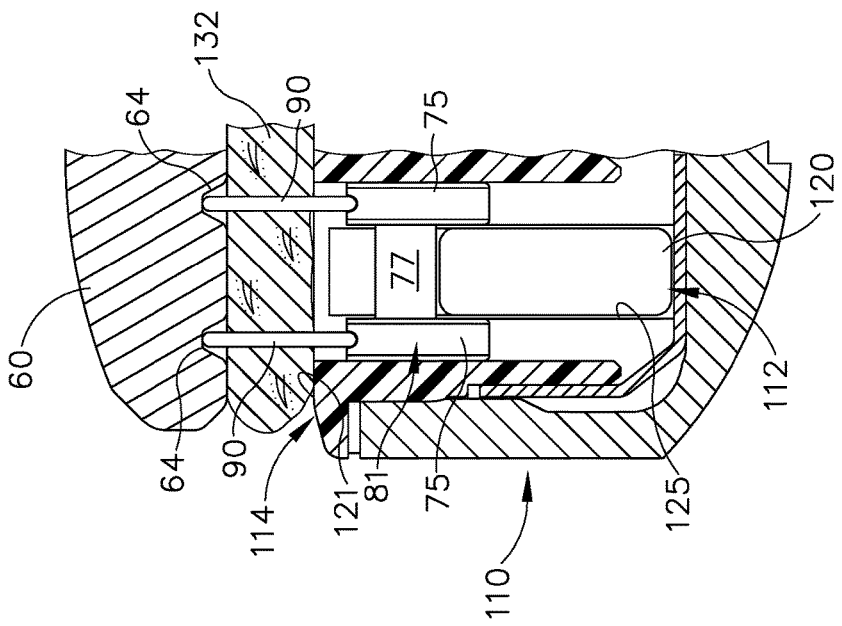
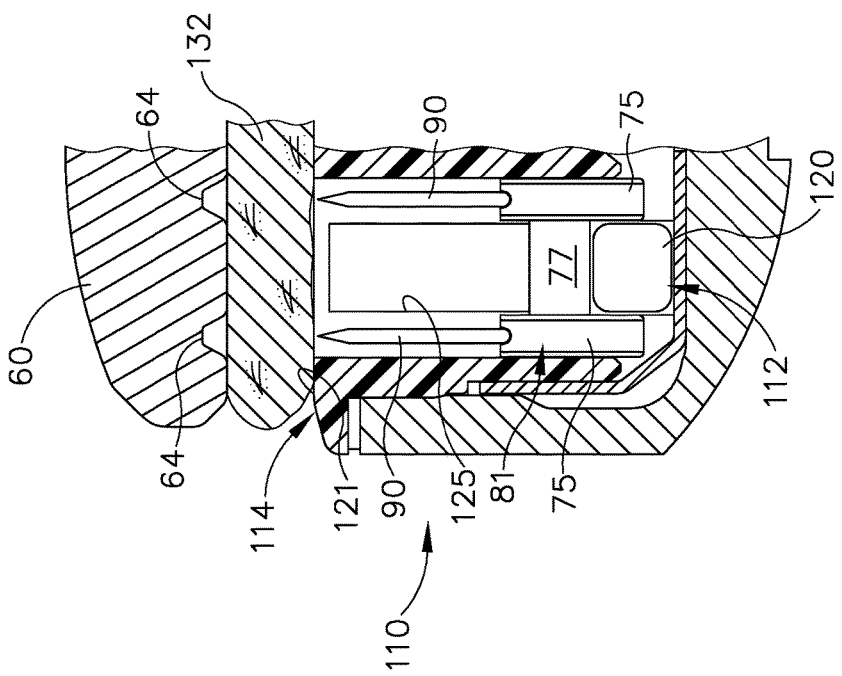

SURGICAL STAPLE CARTRIDGE WITH HYDRAULIC STAPLE DEPLOYMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No.

2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, published as U.S. Pub. No. 2016/0089146 on May 31, 2016. The disclosure of each of the above-cited U.S. patents, U.S. Patent Publications, and U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9A depicts an enlarged cross-sectional view of the end effector of FIG. 8B, taken along section line 9A-9A of FIG. 8B, in the unfired state; and FIG. 9B depicts an enlarged cross-sectional view of the end effector of FIG. 8D, taken along section line 9B-9B of FIG. 8D, in the fired state.

Figure 1:
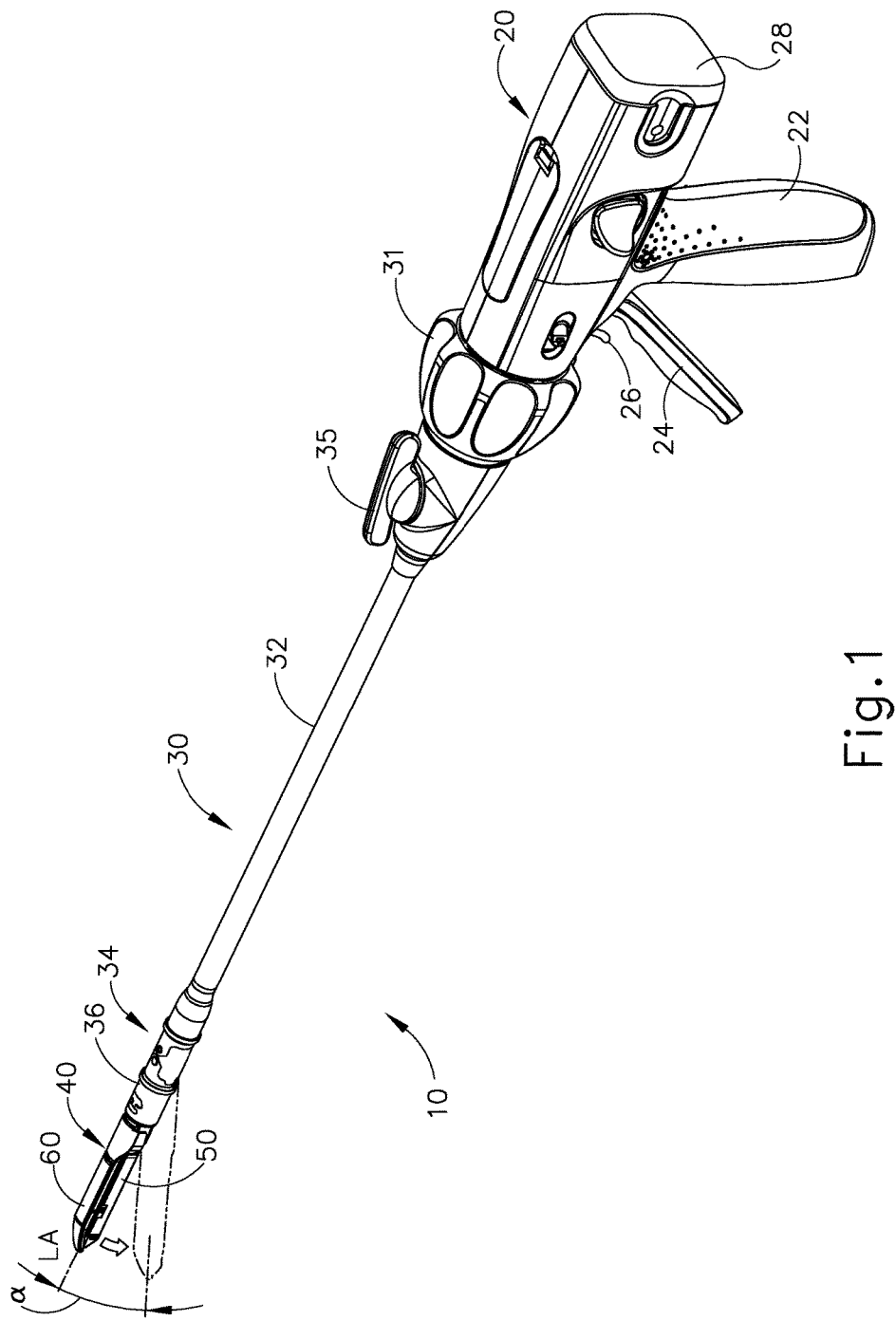
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, surgical instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of surgical instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
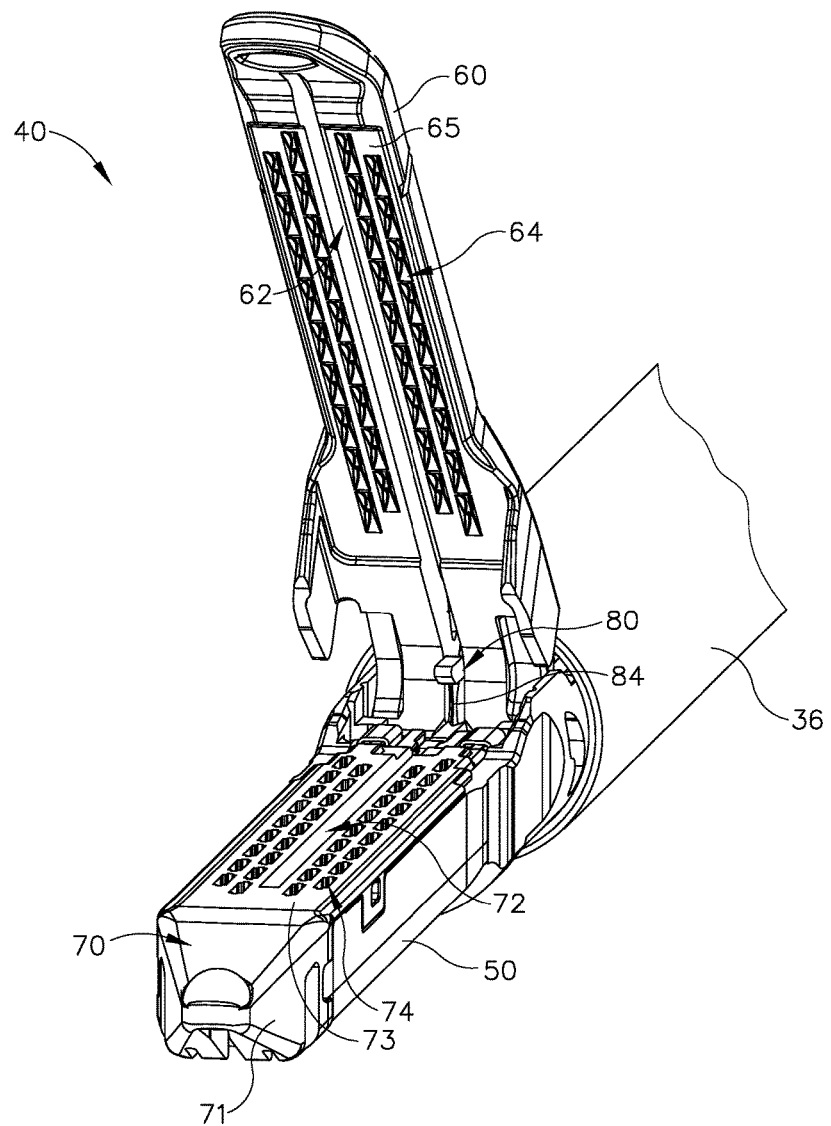
FIG. 2 depicts a perspective view of an end effector of the instrument of FIG. 1, with the end effector in an open configuration showing a first exemplary staple cartridge containing a plurality of staples.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34).

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. Pub. No. 2015/0374360, entitled "Articulation Drive Features for Surgical Stapler," published Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
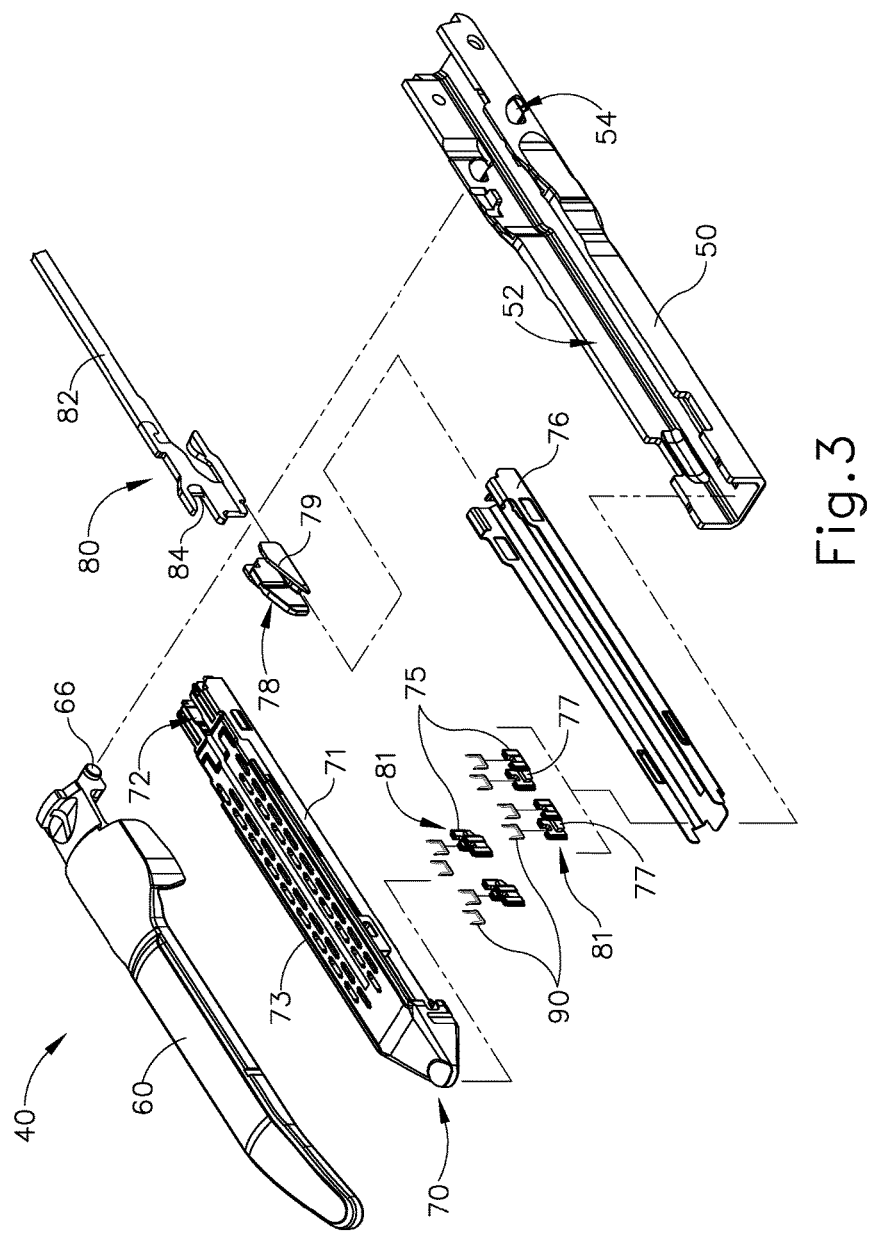
FIG. 3 depicts an exploded perspective view of the end effector and staple cartridge of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a first exemplary staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

In one example, a pair of staple drivers (75) are connected together by a driver cam (77) extending therebetween to form a driver assembly (81). Wedge sled (78) includes a pair of obliquely angled cam surfaces (79), which are configured to engage driver cam (77) and thereby simultaneously drive the connected pair of staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in respective channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. Pub. No. 2015/0374373, entitled "Jaw Opening Feature for Surgical Stapler," published Dec. 31, 2015, the disclosure of which is incorporated by reference herein.

As noted above, handle assembly (20) includes pistol grip (22) and closure trigger (24). As also noted above, anvil (60) is closed toward lower jaw (50) in response to distal advancement of closure ring (36) from an open configuration to a closed configuration with lower jaw (50). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, surgical instrument (10) provides motorized control of firing beam (82). In particular, surgical instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein.

It should also be understood that any other components or features of surgical instrument (10) may be configured and operable in accordance with any of the various references cited herein. Additional exemplary modifications that may be provided for surgical instrument (10) will be described in greater detail below. Various suitable ways in which the below teachings may be incorporated into surgical instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various surgical instruments taught in the various references that are cited herein. It should also be understood that the below teachings are not limited to surgical instrument (10) or devices taught in the references cited herein. The below teachings may be readily applied to various other kinds of surgical instruments, including instruments that would not be classified as surgical staplers. Various other suitable devices and settings in which the below teachings may be applied will be apparent to those of ordinary skill in the art in view of the teachings herein.

II. Exemplary Surgical Stapler with Hydraulic Staple Deployment

In some instances, it may be desirable to equip end effector (40) with a hydraulic system to drive selective movement of staples (90) for forming staples (90) within the tissue captured between anvil (60) and deck (73). Such a hydraulic system may provide equivalent drive forces to each of the staples (90) simultaneously. For example, some tissues may have varying density due to various anatomical structures present within the tissue. Driving staples (90) as discussed above may result in unequal pressure being applied across varyingly dense tissue by staples (90). By contrast, commonly connected hydraulic systems may provide a reactionary force back on the fluid within the hydraulic system at each staple (90). The fluid thus simultaneously acts on each staple (90), directly or indirectly, with an equivalent driving force. Furthermore, such hydraulic systems may include pressure release components to redirect the fluid and reduce driving forces simultaneously across the tissue at each staple (90) in the event that the fluid pressure reaches a threshold value. In other words, the pressure release components may function to limit force applied to the tissue at each staple to inhibit damaging the tissue and/or to prevent rupture of the hydraulic fluid circuit.

In some instances, deck (73) may be further configured to conform to the tissue to further accommodate portions of tissue with varying density; to thereby prevent concentrated forces from damaging the tissue. One such example of a staple cartridge (110) with a hydraulic staple drive system (112) and deformable deck (114) is shown and described below in greater detail. It will be appreciated that alternative hydraulic systems and decks may be used alone or in combination for deploying staples (90). Staple cartridge (110) may also replace staple cartridge (70) described above for use with surgical instrument (10). In other words, staple cartridge (110) of the present example may be readily used with instrument (10). Alternatively, another surgical instrument may be configured to accommodate one or more features of staple cartridge (110).

Figure 4:
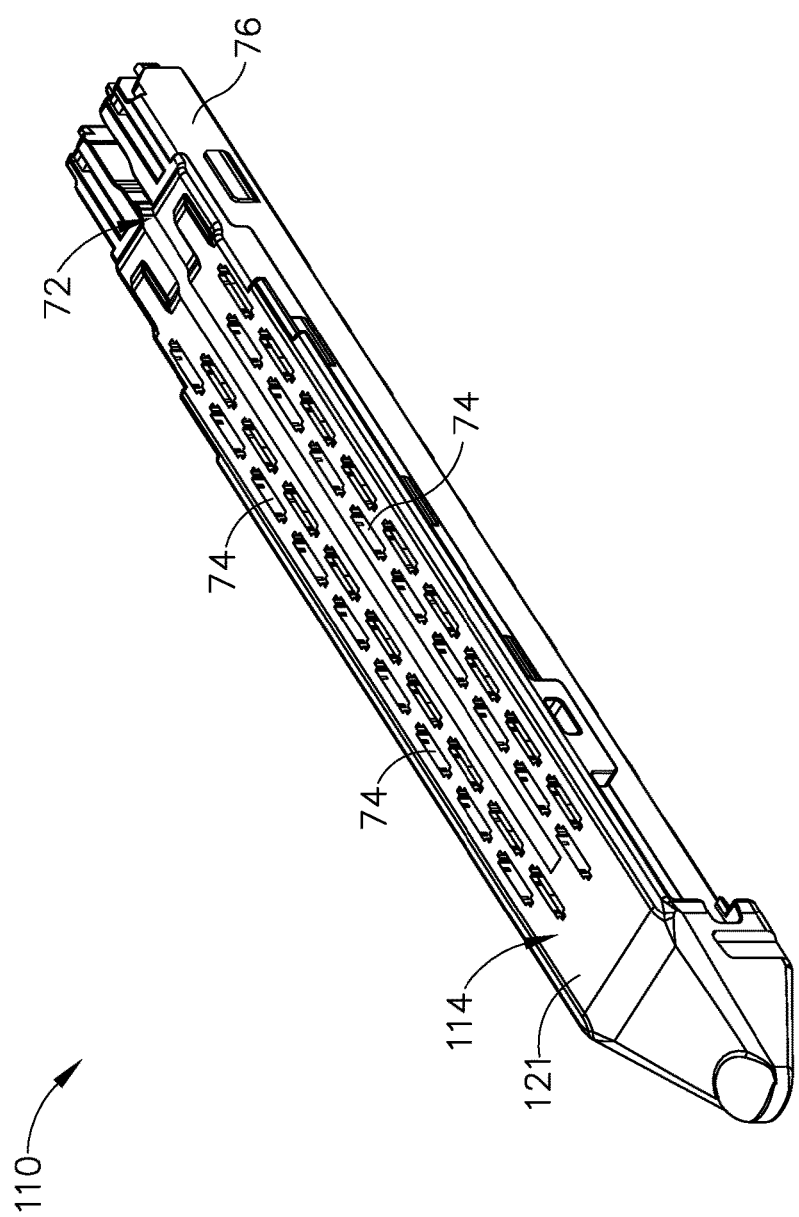
FIG. 4 depicts a perspective view of a second exemplary staple cartridge that may be used with the end effector of FIG. 2.
Figure 5:
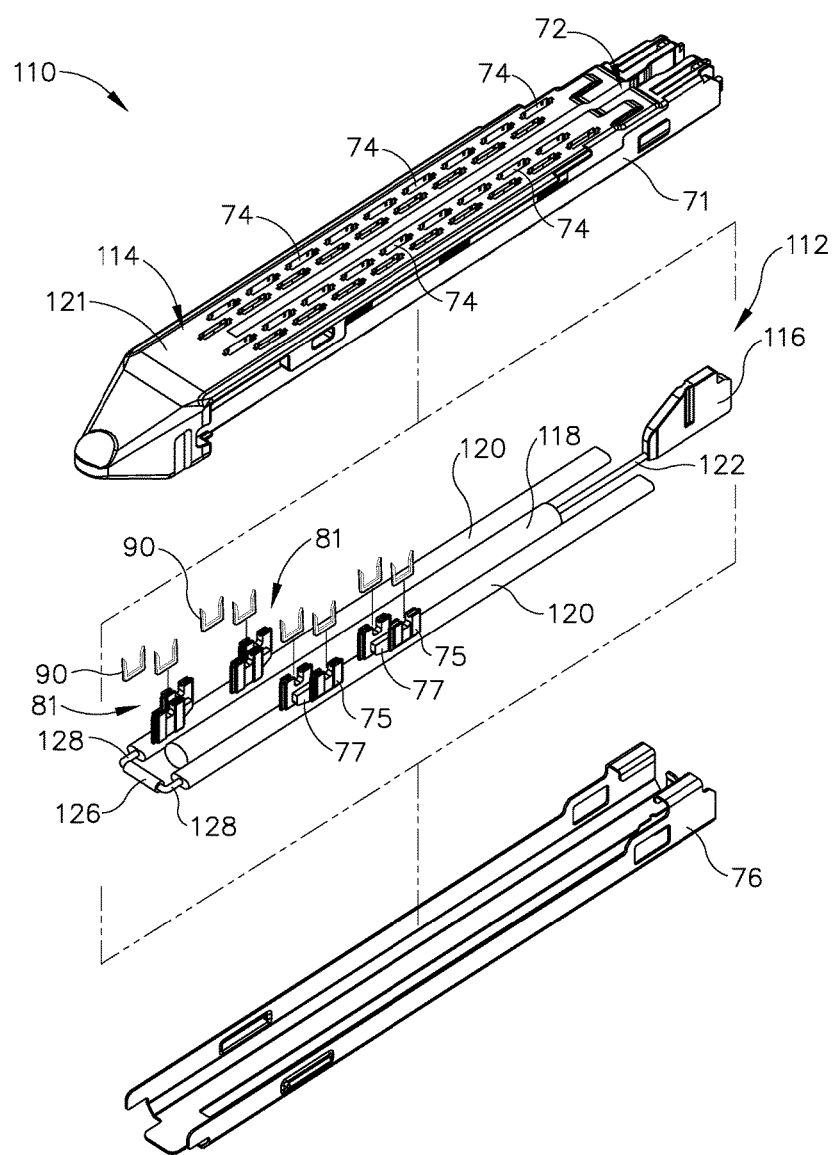
FIG. 5 depicts an exploded perspective view of the staple cartridge of FIG. 4, showing a hydraulic staple drive system.
Figure 6:
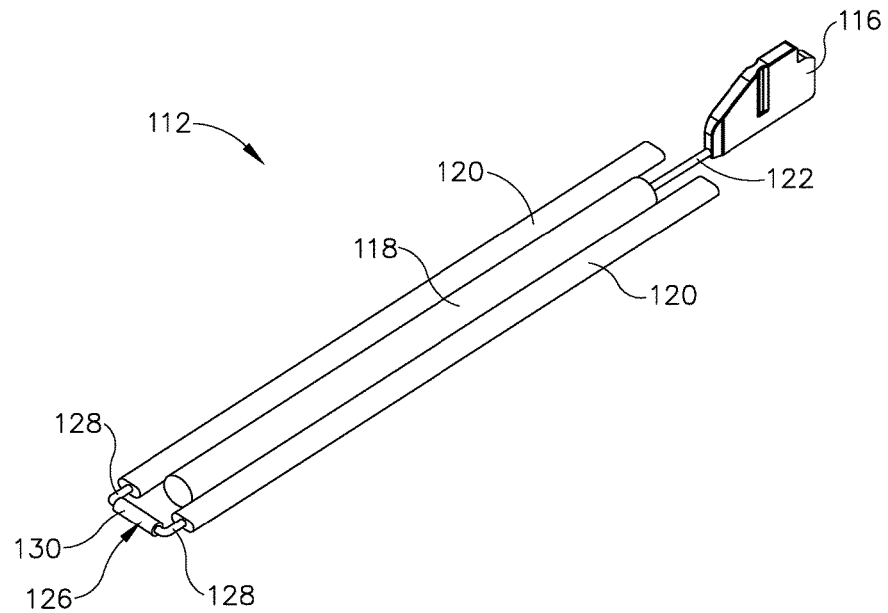
FIG. 6 depicts a perspective view of the hydraulic staple drive system of FIG. 5.

A. Exemplary Hydraulic Staple Cartridge with a Hydraulic Staple Drive System FIGS. 4-5 show staple cartridge (110) having hydraulic staple drive system (112) and deformable deck (114) for equalizing compression forces along tissue while stapling the tissue as discussed above. Staple cartridge (110) includes staples (90) received within respective staple pockets (74) and contained within tray (76) and cartridge body (71) as discussed above. To this end, like numbers represent like features discussed above in greater detail. However, rather than wedge sled (78) (see FIG. 3), hydraulic staple drive system (112) includes a drive sled (116) engaged with a fluid supply cylinder (118) that contains a fluid, such as a liquid. Various suitable fluids that may be used in hydraulic staple drive system (112) will be apparent to those of ordinary skill in the art in view of the teachings herein. Hydraulic staple drive system (112) further includes a pair of hydraulic expandable members, which in the present example are a pair of expandable, elongated balloons (120) that are configured to engage driver assemblies (81). Balloons (120) are thus configured to receive fluid from fluid supply cylinder (118) to expand from a contracted state to an expanded state for driving staples (90) upwardly through tissue and toward anvil (60) for formation in the tissue. In some versions, balloons (120) are extensible in addition to being expandable. In some other versions, balloons (120) are expandable yet non-extensible.

Deformable deck (114) of the present example includes an upper surface (121) that configured to deform under pressure and conform to tissue received thereagainst. Thus, hydraulic drive system (112) and deformable deck (114) are configured to reduce the likelihood of damaging tissue during use.

As shown in FIGS. 5-7A, a proximal portion of drive sled (116) is configured to receive knife member (80) as discussed above with respect to wedge sled (78) (see FIG. 3) to selectively slide drive sled (116) longitudinally from the proximal position toward the distal position. A distal portion of drive sled (116) has a plunger (122) extending distally therefrom into fluid supply cylinder (118). Plunger (122) is slidably disposed in cylinder (118) in the present example, such that distal movement of plunger (122) in cylinder reduces the storage volume available to the fluid contained therein. As the volume in cylinder (118) is reduced, this pressurizes the fluid to force the fluid into each balloon (120) via a pair of respective supply conduits (124). Each balloon (120) thus expands to engage driver assemblies (81) with an expansion force capable of forming staples (90) within the tissue for fluidly sealing the tissue.

While the hydraulic expandable members of the present example are in the form of balloons (120), hydraulic expandable members may alternatively be another kind of expansion member or an expansion assembly, such as a hydraulic piston, configured to elongate in at least one dimension for engaging driver assemblies (81). Thus, the term "hydraulic expandable member" is not intended to be limited to exemplary balloon (120). It should also be understood that plunger (122) and cylinder (118) may be replaced with a variety of alternative structures. By way of example only cylinder (118) may be replaced with a collapsible reservoir, such as a bellows assembly, etc., with a proximal end of the reservoir being secured to the distal portion of drive sled (116). In such versions, drive sled (116) may collapse the reservoir as drive sled (116) is driven distally, thereby pressurizing the fluid in the reservoir to drive the fluid into balloons (120). Other suitable forms of hydraulic expandable members that may be used, and other suitable alternatives to plunger (122) and cylinder (118), will be apparent to those of ordinary skill in the art in view of the teachings herein.

In the present example, each driver assembly (81) straddles one of the balloons (120) such that each balloon (120) engages a driver cam (77). As balloons (120) expand and engage driver cams (77), driver cams (77) simultaneously drive the respective pair of opposing drivers (75) upwardly. As discussed above, staple pockets (74) and staples (90) received therein are arranged in a pair of rows on one lateral side of channel (72) and another pair of rows on another lateral side of channel (72). Thus, exemplary staple drive system (112) of the present example has elongated balloons (120) within expander channels (125) (see FIGS. 9A-9B) directly below driver cams (77) on each lateral side of channel (72). However, balloons (120) may be alternatively configured to have more or fewer hydraulic expandable members, such as balloons (120). For example, hydraulic staple drive system (112) may alternatively include an individual balloon for each respective driver cam (77); or even each respective driver (75) in case driver cam (77) is omitted. Hydraulic expandable members of any type may thus be in any desirable arrangement to accommodate any variety of desirable staple patterns in deck (114).

Fluid supply cylinder (118) of the present example is generally a tubular and rigid structure that is configured to receive plunger (122) of drive sled (116). More particularly, plunger (122) provides a piston structure that fluidly seals against an inner surface of fluid supply cylinder (118) such that distal movement of plunger (122) effectively collapses the portion of the fluid supply cylinder (118) containing the fluid for discharging the fluid into balloons (120). In order to accommodate movement of drive sled (116), the distal end portion of drive sled (116) is configured to cut and pass through fluid supply cylinder (118) to allow for a full distal stroke of drive sled (116). Alternatively, fluid supply cylinder (118) may be relatively flexible. For example, the distal end portion of drive sled (116) may effectively collapse the entirety of fluid supply cylinder (118) such that a distal end of fluid supply cylinder (118) is squeezed toward a proximal end of fluid supply cylinder (118). The term "collapse" is thus intended to be any reduction of volume containing the fluid and is not intended to be limited to exemplary fluid supply cylinder (118).

Given that knife member (80) forces drive sled (116) distally one full stroke from the unfired position to the fired position, plunger (122) generally discharges the entirety of fluid from fluid supply cylinder (118). However, the entirety of the fluid may not be needed to deploy staples (90) and, in fact, may overfill balloons (120) beyond a predetermined maximum expansion force. Hydraulic staple drive system (112) is thus further configured to limit the expansion force to the predetermined maximum expansion force via a pressure relief reservoir (126). More particularly, pressure relief reservoir (126) fluidly connects to each balloon (120) via a pair of relief conduits (228) that respectively extend therebetween. Once balloons (120) reach the predetermined maximum expansion force, relief conduits (228) direct excess fluid into pressure relief reservoir (126) until pressure applied to the fluid in balloons (120) decreases below the predetermined maximum expansion force.

Exemplary pressure relief reservoir (126) includes a resilient body (130), such as another balloon, that is configured to expand from a contracted state to an expanded state. The resiliency of body (130) is tuned to the predetermined maximum expansion force such that balloons (120) generally initiate expansion under a lower pressure than resilient body (130). However, once the fluid pressure within balloons (120) increases to the predetermined maximum expansion force, resilient body (130) of pressure relief reservoir (126) begins to expand from its contracted state to limit pressure in balloons (120). In the present example, body (130) is extensible and thus the extensible resilience of body (130) defines the pressure threshold at which body (130) will begin to expand. In some other versions, body (130) is non-extensible but a resilient member (e.g., leaf spring, stent-like cage, etc.) is engaged with body; and the resilience of the resilient member defines the pressure threshold at which body (130) will begin to expand. Other suitable ways in which resilient body (130) may be configured to only expand after the fluid pressure reaches a predetermined threshold value will be apparent to those of ordinary skill in the art in view of the teachings herein. It should also be understood that one or more pressure sensitive valves (e.g., interposed between relief conduits (228) and pressure relief reservoir (126)) may be used to establish a threshold fluid pressure value to selectively provide pressure relief to balloons (120). Pressure relief reservoir (126) is thus not intended to be unnecessarily limited to the example described herein.

It should be understood from the foregoing that, in the event that fluid flow from fluid supply cylinder (118) or additional downward force is applied to staples (90), resilient body (130) will expand to maintain the pressure of the predetermined maximum expansion force within balloons (120). In the event that forces acting on balloons (120) reduce decrease after expansion of pressure relief reservoir (126), resilient body (130) contracts to maintain the predetermined maximum expansion force until resilient body (130) returns to the contracted state. Once resilient body (130) returns to the contracted state, the expansion force of balloons (120) may then decrease below the predetermined maximum expansion force. Pressure relief reservoir (126) is thus configured to limit the expansion force of the balloons (120) to less than or equal to the predetermined maximum expansion force to inhibit damaging the tissue.

It should be understood from the foregoing that staple cartridge (110) of the present example contains a closed hydraulic circuit. This hydraulic circuit is formed by cylinder (118), balloons (120), conduits (124, 128), and resilient body (130). The closed nature of this hydraulic circuit enables staple cartridge (110) to be used in a conventional end effector such as end effector (40). In other words, staple cartridge (110) does not need to be coupled with an external source of fluid, such as a fluid source contained in handle assembly (20).

B. Exemplary Actuation of End Effector Including a Hydraulic Staple Cartridge

Figure 7A:
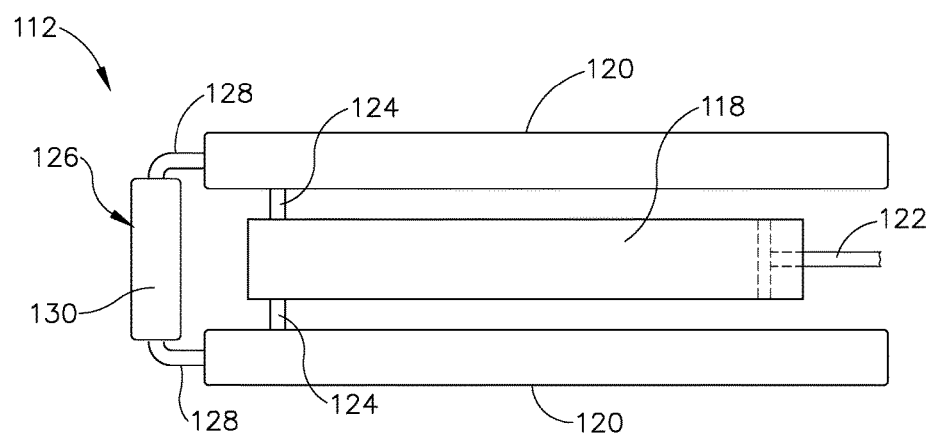
FIG. 7A depicts a top plan view of the hydraulic staple drive system of FIG. 5 in an unfired state prior to deploying staples.
Figure 7B:
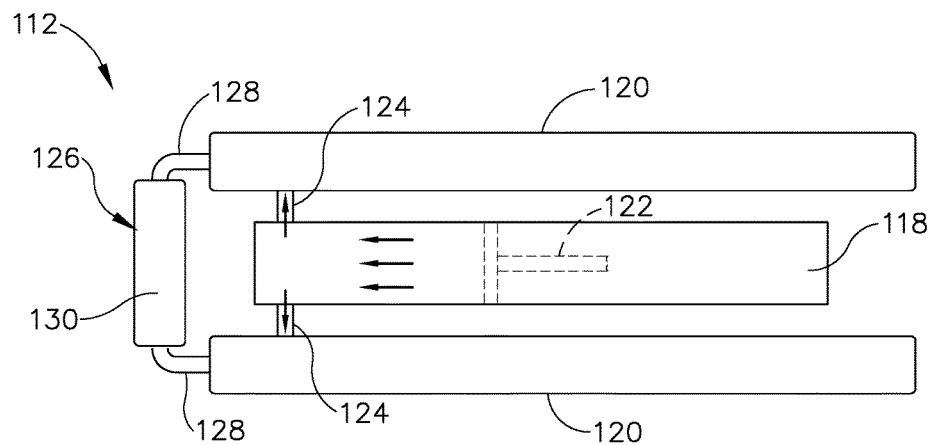
FIG. 7B depicts a top plan view of the hydraulic staple drive system of FIG. 5, showing the hydraulic staple drive system in a staple deploying state.
Figure 7C:
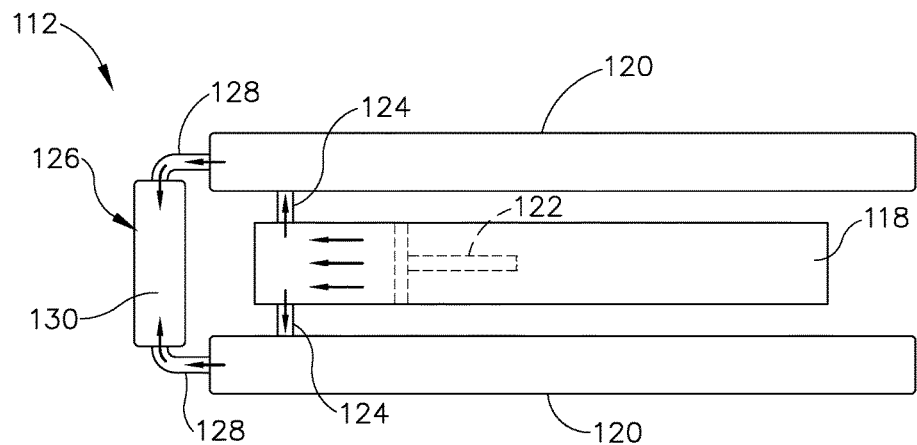
FIG. 7C depicts a top plan view of the hydraulic staple drive system of FIG. 5, showing the hydraulic staple drive system limiting deployment of the staples.

In use, staple drive system (112) of the present example contains fluid within fluid supply cylinder (118) as shown in FIGS. 7A-7C. Alternatively, balloons (120) may fluidly connect to another fluid source, such as a fluid source in handle assembly (not shown). As shown in FIG. 7B, the user selectively fires knife member (80) to distally slide plunger (122) of drive sled (116) and begin collapsing the portion of fluid supply cylinder (118) containing the fluid. The fluid, now pressurized, flows through supply conduits (124) and into respective balloons (120) to initiate expansion of balloons (120) from the contracted state to the expanded state for deploying staples (90) (see FIG. 5). Balloons (120) expand until reaching the maximum predetermined expansion force such that excess fluid flows from each balloon (120) through relief conduits (128) and into pressure relief reservoir (126) as shown in FIG. 7C. Such fluid flow may continue until plunger (22) completes its full stroke and reaches the distal position. While fluid flows to pressure relief reservoir (126) via balloons (120), it will be appreciated that alternative flow arrangements may configured to fluidly connect pressure relief reservoir (126), balloons (120), and any one of a variety of fluid sources. To this end, the invention is not intended to be unnecessarily limited to the particular fluid connections described above and may be any operative fluid connection.

Figure 8A:
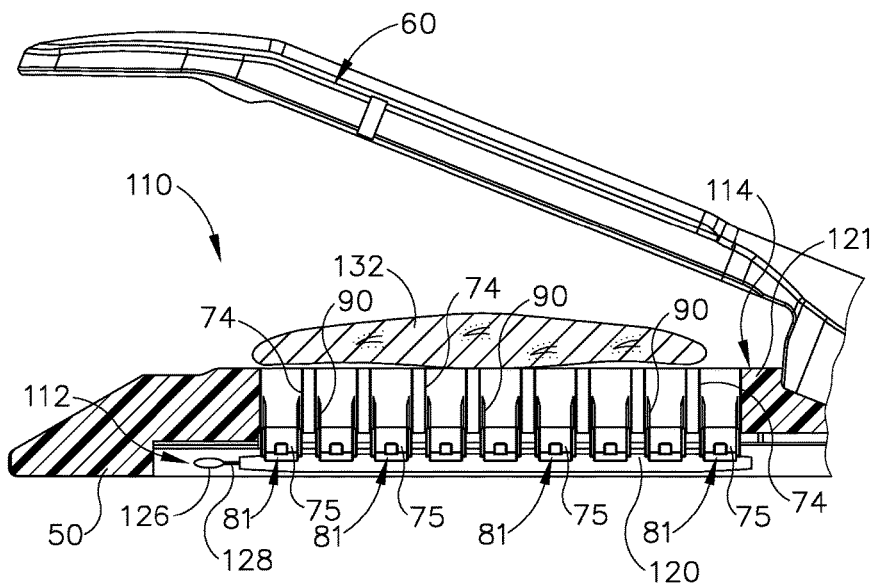
FIG. 8A depicts a side view of the end effector of FIG. 2 with the staple cartridge of FIG. 4, with the end effector in an open configuration receiving tissue.
Figure 8B:
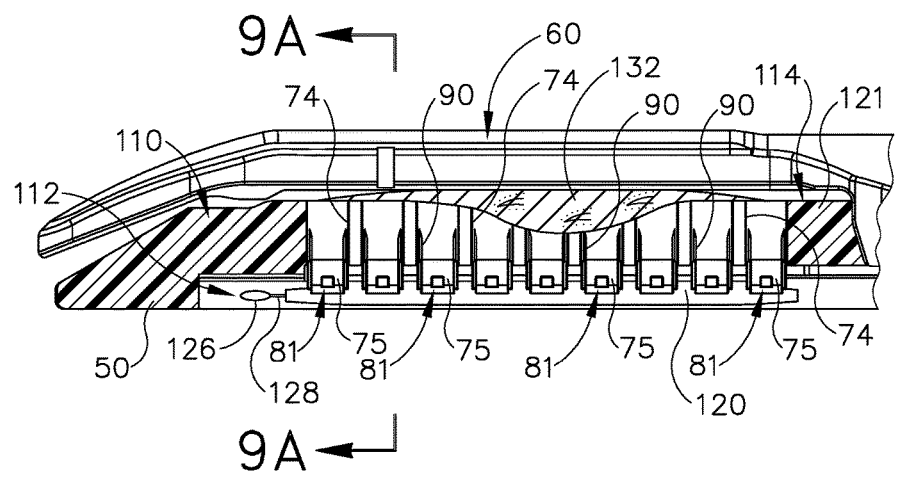
FIG. 8B depicts a side view of the end effector of FIG. 2 with the staple cartridge of FIG. 4, with the end effector in a closed configuration after having received the tissue, in the unfired state.
Figure 8C:
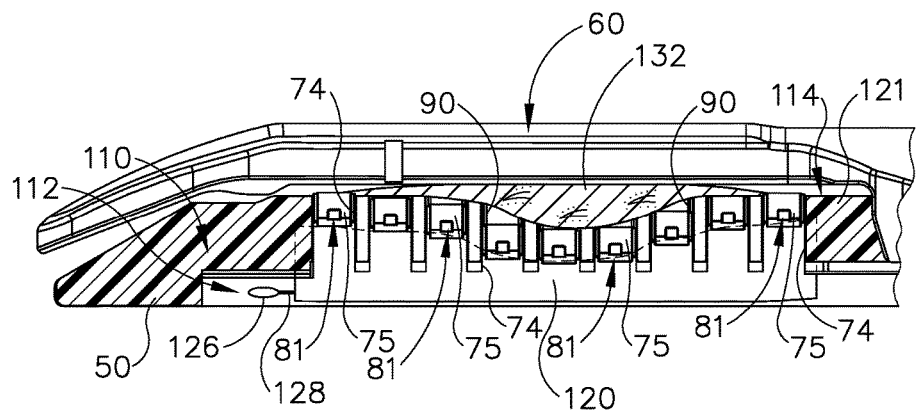
FIG. 8C depicts a side view of the end effector of FIG. 2 with the staple cartridge of FIG. 4, with the hydraulic staple drive system deploying the staples.

As shown in FIG. 8A, anvil (60) and upper surface receive a patient's tissue (132) while anvil (60) is in the open position. As shown in FIG. 8B, closing anvil (60) toward lower jaw (50) compresses tissue (132) against deck (114) in the closed configuration such that upper surface (114) deforms to conform to the varying density present in tissue (132) to apply a relatively equal amount of pressure along tissue (132). In the closed configuration, the user then selectively fires knife member (80) to actuate hydraulic drive system (112) as discussed above. To this end, balloons (120) expand with the expansion force from the fluid to direct driver assemblies (81) upwardly and toward tissue (132), as shown in FIG. 8C.

Figure 8D:
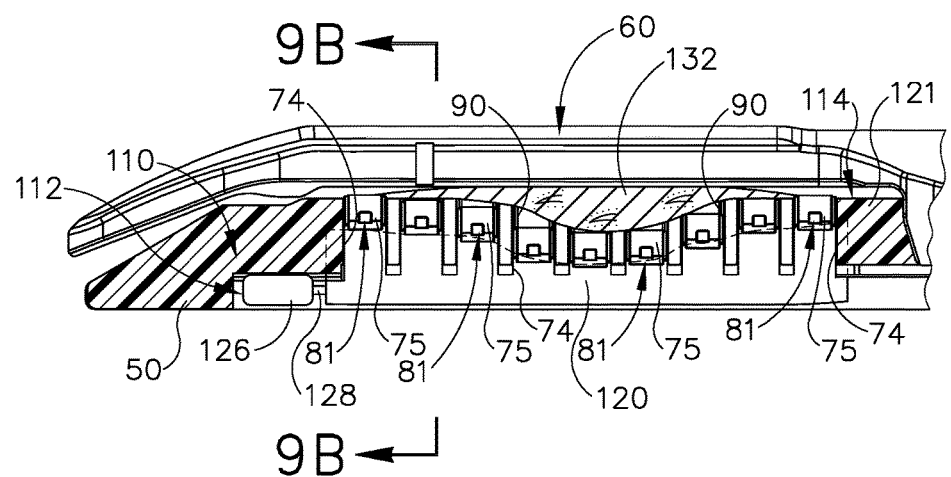
FIG. 8D depicts a side view of the end effector of FIG. 2 with the staple cartridge of FIG. 4, with the hydraulic staple drive system in a fired state.

With drivers (75) and staples (90) being supported on fluidly connected balloons (120), each driver (75) is directed upwardly with equivalent expansion force since pressure from reaction forces of drivers (75) will distribute evenly throughout the fluid. Thus, regardless of the amount of upward travel of driver assemblies (81), each staple (90) will puncture tissue (132) and form within tissue (132) with equivalent force. Expansion forces on drivers (75) will continue to increase throughout the distal stroke of plunger (122) (see FIG. 7C) until the expansion force reaches the maximum predetermined expansion force threshold. Pressure relief reservoir (126) will then receive the excess fluid as shown in FIG. 8D and discussed above to limit the amount of pressure applied to tissue (132), and to limit the amount of pressure within the hydraulic circuit.

FIGS. 9A-9B show exemplary balloon (120) respectively in contracted and expanded states contained with expander channel (125). Whereas expander channel (125) previously received wedge sled (78) (see FIG. 3) to direct driver assembly (81) upwardly, balloon (120) expands within expander channel (125) toward the expanded state to direct driver assembly (81) upwardly. Thereby, staple (90) is formed between driver (75) and anvil (60) to form staple (90) within tissue (132) and fluidly seal tissue (132) immediately before knife member (80) cuts tissue (132).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly; (b) a shaft assembly extending distally from the body assembly; and (c) an end effector extending distally from the shaft assembly, wherein the end effector includes: (i) a first jaw having an anvil, wherein the anvil is configured to form a plurality of staples received thereagainst, (ii) a second jaw, wherein the first jaw is movable relative to the second jaw from an open configuration toward a closed configuration for capturing the tissue therebetween and forming the staples therein, and (iii) a staple cartridge received by the second jaw, wherein the staple cartridge includes: (A) the plurality of staples, and (B) a hydraulic expandable member configured to receive a fluid, wherein the hydraulic expandable member is configured to expand from a contracted state toward an expanded state upon receiving the fluid, and wherein the hydraulic expandable member is configured to direct at least one of the plurality of staples toward the anvil for forcing the at least one of the plurality of staples against the anvil and forming the at least one of the plurality of staples within the tissue.

Example 2

The surgical instrument of claim 1, wherein the staple cartridge further includes a deck having a plurality of staple pockets extending therethrough.

Example 3

The surgical instrument of claim 2, wherein an upper surface of the deck is configured to deform upon receiving the tissue thereagainst with the anvil in the closed configuration.

Example 4

The surgical instrument of claim 1, wherein the hydraulic expandable member comprises at least one expandable bladder.

Example 5

The surgical instrument of claim 4, wherein the at least one expandable bladder is comprises a first expandable balloon.

Example 6

The surgical instrument of claim 5, wherein the staple cartridge further includes a second expandable balloon, wherein the plurality of staples includes a first row of staples and a second row of staples, and wherein the first and second expandable balloons are aligned with the first and second rows of staples, respectively, such that the first and second expandable balloons are expandable from the contracted state toward the expanded state to respectively direct the first and second rows of staples toward the anvil.

Example 7

The surgical instrument of claim 1, wherein the hydraulic expandable member is configured to expand from the contracted state toward the expanded state with an expansion force less than or equal to a predetermined maximum expansion force for limiting the expansion force applied to the at least one of the plurality of staples.

Example 8

The surgical instrument of claim 7, wherein the staple cartridge further includes a reservoir fluidly connected to the hydraulic expandable member, and wherein the reservoir is configured to receive the fluid when the hydraulic expandable member expands with the predetermined maximum expansion force and thereby limit the fluid accumulating within the hydraulic expandable member for limiting the expansion force applied to the at least one of the plurality of staples.

Example 9

The surgical instrument of claim 8, wherein the reservoir includes a body configured to resiliently expand to collect the fluid and thereby limit the fluid accumulating within the hydraulic expandable member.

Example 10

The surgical instrument of claim 9, wherein the body of the reservoir is configured to resiliently expand and resiliently contract to limit the expansion force of the hydraulic expandable member to be less than or equal to the predetermined maximum expansion force.

Example 11

The surgical instrument of claim 1, wherein the staple cartridge further includes a fluid supply cylinder containing a fluid.

Example 12

The surgical instrument of claim 11, wherein the end effector includes a firing member configured to be selectively driven from an unfired position to a fired position, and wherein the firing member is configured to be selectively driven from the unfired position toward the fired position to direct the fluid from the fluid supply cylinder toward the hydraulic expandable member and expand the hydraulic expandable member from the contracted state toward the expanded state.

Example 13

The surgical instrument of claim 12, wherein the firing member is configured to collapse at least a portion of the fluid supply cylinder containing the fluid and thereby force the fluid from the fluid supply cylinder toward the hydraulic expandable member as the firing member is driven from the unfired position toward the fired position.

Example 14

The surgical instrument of claim 13, wherein the staple cartridge further includes a sled engaged with the fluid supply cylinder and configured to slide from a proximal position toward a distal position, wherein the sled is configured to receive the firing member directly thereagainst such that the firing member is configured to selectively slide the sled from the proximal position to the distal position for collapsing the fluid supply cylinder therewith.

Example 15

The surgical instrument of claim 1, wherein the hydraulic expandable member is configured to expand from the contracted state toward the expanded state with an expansion force that operatively drives the at least one staple toward the anvil, and wherein the staple cartridge is configured to direct each of the plurality of staples toward the anvil with equivalent expansion force.

Example 16

A staple cartridge for a surgical instrument, comprising: (a) a cartridge body configured to be received by the surgical instrument; (b) a plurality of staples positioned within the cartridge body; and (c) a closed hydraulic circuit within the cartridge body, wherein the closed hydraulic circuit comprises a hydraulic expandable member positioned within the cartridge body and configured to receive a fluid, wherein the hydraulic expandable member is configured to expand from a contracted state toward an expanded state upon receiving the fluid, and wherein the hydraulic expandable member is configured to direct at least one of the plurality of staples from the cartridge body for forcing the at least one of the plurality of staples against an anvil and forming the staple.

Example 17

The surgical instrument of claim 16, wherein the hydraulic expandable member is configured to expand from the contracted state toward the expanded state with an expansion force less than or equal to a predetermined maximum expansion force for limiting the expansion force applied to the at least one of the plurality of staples.

Example 18

The surgical instrument of claim 1, wherein closed hydraulic circuit further includes a fluid supply cylinder positioned within the cartridge body, and wherein the fluid supply cylinder contains a fluid.

Example 19

A method of stapling tissue with a surgical instrument having a staple cartridge, wherein the staple cartridge includes a cartridge body, a plurality of staples, and a hydraulic expandable member, wherein the hydraulic expandable member is positioned within the cartridge body and configured to receive a fluid, wherein the hydraulic expandable member is configured to expand from a contracted state toward an expanded state upon receiving the fluid, and wherein the hydraulic expandable member is configured to direct at least one of the plurality of staples from the cartridge body for forcing the at least one of the plurality of staples against an anvil and forming the staple, the method comprising: (a) introducing the fluid into the hydraulic expandable member in order to expand the hydraulic expandable member from the contracted state toward the expanded state; and (b) deploying at least one of the plurality of staples toward the anvil via the hydraulic expandable member to form the at least one of the plurality of staples.

Example 20

The method of claim 19, further comprising simultaneously applying equivalent force to each of the plurality of staples that are being deployed toward the anvil.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Oct. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument, comprising:
   (a) a body assembly;
   (b) a shaft assembly extending distally from the body assembly; and
   (c) an end effector extending distally from the shaft assembly, wherein the end effector includes:
      (i) a first jaw having an anvil, wherein the anvil is configured to form a plurality of staples received thereagainst,
      (ii) a second jaw, wherein the first jaw is movable relative to the second jaw from an open configuration toward a closed configuration for capturing the tissue therebetween and forming the staples therein, and
      (iii) a staple cartridge received by the second jaw, wherein the staple cartridge includes:
         (A) the plurality of staples,
         (B) a translating member, and
         (C) a hydraulic expandable member configured to receive a fluid and expand from a contracted state toward an expanded state to direct at least one of the plurality of staples toward the anvil for forming the at least one staple, wherein the hydraulic expandable member is configured to expand toward the expanded state in response to distal translation of the translating member through the staple cartridge.

2. The surgical instrument of claim 1, wherein the staple cartridge further includes a deck having a plurality of staple pockets extending therethrough.

3. The surgical instrument of claim 2, wherein an upper surface of the deck is configured to deform upon receiving the tissue thereagainst with the anvil in the closed configuration.

4. The surgical instrument of claim 1, wherein the hydraulic expandable member comprises at least one expandable bladder.

5. The surgical instrument of claim 4, wherein the at least one expandable bladder comprises a first expandable balloon.

6. The surgical instrument of claim 5, wherein the staple cartridge further includes a second expandable balloon, wherein the plurality of staples includes a first row of staples and a second row of staples, and wherein the first and second expandable balloons are aligned with the first and second rows of staples, respectively, such that the first and second expandable balloons are expandable from the contracted state toward the expanded state to respectively direct the first and second rows of staples toward the anvil.

7. The surgical instrument of claim 1, wherein the hydraulic expandable member is configured to expand from the contracted state toward the expanded state with an expansion force less than or equal to a predetermined maximum expansion force for limiting the expansion force applied to the at least one of the plurality of staples.

8. The surgical instrument of claim 7, wherein the staple cartridge further includes a reservoir fluidly connected to the hydraulic expandable member, and wherein the reservoir is configured to receive the fluid when the hydraulic expandable member expands with the predetermined maximum expansion force and thereby limit the fluid accumulating within the hydraulic expandable member for limiting the expansion force applied to the at least one of the plurality of staples.

9. The surgical instrument of claim 8, wherein the reservoir includes a body configured to resiliently expand to collect the fluid and thereby limit the fluid accumulating within the hydraulic expandable member.

10. The surgical instrument of claim 9, wherein the body of the reservoir is configured to resiliently expand and resiliently contract to limit the expansion force of the hydraulic expandable member to be less than or equal to the predetermined maximum expansion force.

11. The surgical instrument of claim 1, wherein the staple cartridge further includes a fluid supply cylinder containing a fluid.

12. The surgical instrument of claim 11, wherein the end effector includes a firing member configured to be selectively driven from an unfired position to a fired position, and wherein the firing member is configured to be selectively driven from the unfired position toward the fired position to direct the fluid from the fluid supply cylinder toward the hydraulic expandable member and expand the hydraulic expandable member from the contracted state toward the expanded state.

13. The surgical instrument of claim 12, wherein the firing member is configured to collapse at least a portion of the fluid supply cylinder containing the fluid and thereby force the fluid from the fluid supply cylinder toward the hydraulic expandable member as the firing member is driven from the unfired position toward the fired position.

14. The surgical instrument of claim 13, wherein the staple cartridge further includes a sled engaged with the fluid supply cylinder and configured to slide from a proximal position toward a distal position, wherein the sled is configured to receive the firing member directly thereagainst such that the firing member is configured to selectively slide the sled from the proximal position to the distal position for collapsing the fluid supply cylinder therewith.

15. The surgical instrument of claim 1, wherein the hydraulic expandable member is configured to expand from the contracted state toward the expanded state with an expansion force that operatively drives the at least one staple toward the anvil, and wherein the staple cartridge is configured to direct each of the plurality of staples toward the anvil with equivalent expansion force.

16. The surgical instrument of claim 1, wherein the translating member supports a cutting member, wherein the cutting member is configured to cut tissue captured between the first and second jaws in response to distal translation of the translating member through the staple cartridge.

17. A staple cartridge for a surgical instrument, comprising:
   (a) a cartridge body configured to be received by the surgical instrument;
   (b) a plurality of staples positioned within the cartridge body; and
   (c) a closed hydraulic circuit within the cartridge body, wherein the closed hydraulic circuit comprises:
      (i) a hydraulic expandable member positioned within the cartridge body and configured to receive a fluid, wherein the hydraulic expandable member is configured to expand from a contracted state toward an expanded state upon receiving the fluid to direct at least one of the plurality of staples from the cartridge body and against an anvil for forming the staple, and (ii) a pressure relief reservoir fluidly coupled with the hydraulic expandable member, wherein the pressure relief reservoir is configured to receive fluid from the hydraulic expandable member and thereby maintain a predetermined maximum fluid pressure within the hydraulic expandable member to limit an expansion force applied to the at least one staple.

18. The staple cartridge of claim 17, wherein the hydraulic expandable member is configured to expand from the contracted state toward the expanded state with an expansion force less than or equal to a predetermined maximum expansion force for limiting the expansion force applied to the at least one of the plurality of staples.

19. The staple cartridge of claim 17, wherein the closed hydraulic circuit further includes a fluid supply cylinder positioned within the cartridge body, and wherein the fluid supply cylinder contains a fluid.

20. A surgical instrument, comprising:
(a) a body assembly;
(b) a shaft assembly extending distally from the body assembly; and
(c) an end effector extending distally from the shaft assembly, wherein the end effector includes:
  (i) a first jaw having an anvil,
  (ii) a second jaw configured to receive a staple cartridge having a plurality of staples, wherein the first jaw is moveable relative to the second jaw for capturing tissue therebetween,
  (iii) a translating member configured to translate longitudinally through the staple cartridge, and
  (iv) an expandable member operatively coupled with the translating member, wherein the expandable member is configured to expand and thereby drive at least one of the staples from the staple cartridge toward the anvil in response to distal translation of the translating member through the staple cartridge.

* * * * *